United States Patent
Bieger et al.

(10) Patent No.: US 6,926,709 B2
(45) Date of Patent: Aug. 9, 2005

(54) FULLY AUTOMATIC, ROBOT-ASSISTED CAMERA GUIDANCE SYSTEM EMPLOYING POSITION SENSORS FOR LAPAROSCOPIC INTERVENTIONS

(75) Inventors: Johannes Bieger, München (DE); Rainer Graumann, Höchstadt (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 141 days.

(21) Appl. No.: 10/276,355

(22) PCT Filed: May 17, 2001

(86) PCT No.: PCT/DE01/01886

§ 371 (c)(1),
(2), (4) Date: Nov. 13, 2002

(87) PCT Pub. No.: WO01/89405

PCT Pub. Date: Nov. 29, 2001

(65) Prior Publication Data

US 2004/0015053 A1 Jan. 22, 2004

(30) Foreign Application Priority Data

May 22, 2000 (DE) .......................................... 100 25 085

(51) Int. Cl.⁷ ............................................... A61B 1/04
(52) U.S. Cl. ............................ 606/1; 600/102; 600/117; 600/118
(58) Field of Search .............................. 606/1; 600/102, 600/117, 118; 382/152–154, 164, 165, 128, 282, 291; 348/71, 65, 169–172

(56) References Cited

U.S. PATENT DOCUMENTS

| 5,368,015 A | 11/1994 | Wilk |
| 5,558,619 A | 9/1996 | Kami et al. |
| 5,749,362 A | 5/1998 | Funda et al. |
| 5,820,545 A | 10/1998 | Arbter et al. |

FOREIGN PATENT DOCUMENTS

| WO | WO 97/29709 | 8/1997 |
| WO | WO 97/29710 | 8/1997 |

OTHER PUBLICATIONS

"Computer Assisted Medical Interventions," Cinquin et al., IEEE Engineering in Medicine and Biology, May/Jun. 1995, pp. 254, 263.

Primary Examiner—Beverly M. Flanagan
(74) Attorney, Agent, or Firm—Schiff Hardin LLP

(57) ABSTRACT

In a method and operating system for conducting a surgical intervention, respective position sensors are mounted at a laparoscope and a surgical instrument used to conduct the intervention, and a navigation system is supplied with orientation information from these position sensors. Based on this orientation information, the navigation system automatically controls a robot arm, to which the laparoscope is mounted, to always maintain the surgical instrument in the field of view of the laparoscope.

5 Claims, 1 Drawing Sheet

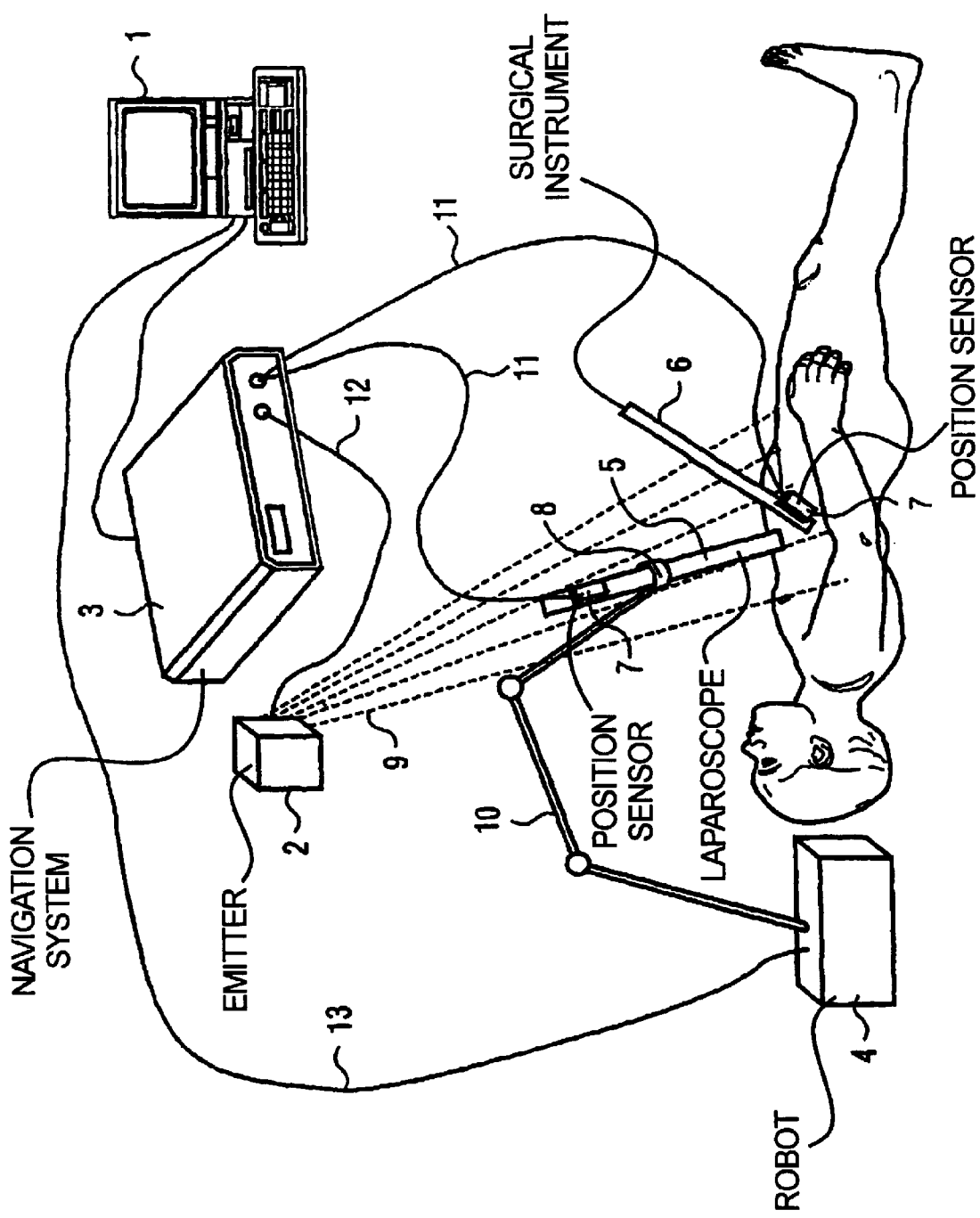

FULLY AUTOMATIC, ROBOT-ASSISTED CAMERA GUIDANCE SYSTEM EMPLOYING POSITION SENSORS FOR LAPAROSCOPIC INTERVENTIONS

BACKGROUND OF THE INVENTION

1. Field of the Invention

The present invention is directed to an operating system for the implementation of surgical interventions, and to a method for monitoring and adjusting a laparoscope attached to a robot arm for the visualization of surgical interventions.

2. Description of the Prior Art

Minimally invasive surgery is gaining more and more significance as an alternative to an open surgical intervention. Such interventions are methods wherein operations are implemented with the smallest possible surgical wounds.

In specific fields of this minimally invasive surgery, for example in laparoscopic interventions wherein instruments are introduced into the abdominal region of the patient through small entry openings and are guided and operatively utilized therein by a surgeon, there is the necessity that the instruments be visualized on an external picture screen with a camera (laparoscope) additionally introduced into the abdominal region. For example, the operating technique is currently routinely utilized in the resection of the gallbladder. The surgeon thereby monitors the movement of the instruments only via the picture screen.

Conventionally, the camera is guided during the intervention by an operating (OP) assistant, who assists the surgeon. In addition to the need for additional personnel and the costs that are thereby incurred, the following problems arise due to the manual camera guidance:

The surgeon and the assistant guiding the camera must collaborate in the closest possible proximity and with the utmost degree of consultation during the operation. The assistant must often work predictively since he/she must not only acquire the current position of instruments but must also support the planned instrument guidance of the surgeon.

The camera guidance becomes imprecise and restless given flagging attention and fatigue on the part of the assistant, particularly given operating procedures that last a long time. Further, the instructions that the surgeon gives the camera-guiding OP assistant must be very precise. These instructions can sometimes be misinterpreted.

Moreover, camera guidance generally does not require any highly qualified training, so that many operating assistants are not enthusiastic about doing this type of assistance.

One approach for minimizing the described problems is the camera with instrument mounts. However, the need for follow-up of the camera by an OP assistant during the operation still is not eliminated.

The use of a robot with which the laparoscope is interactively controlled and moved by the surgeon is also known. Given this method, however, the surgeon must additionally concentrate on the control of the camera.

Another approach is disclosed by U.S. Pat. No. 5,820,545, "Method of Tracking a Surgical Instrument with a Mono or Stereo Laparoscope". The surgical instruments introduced into the body are thereby provided with color-coded markings. These markings are detected by the camera introduced into the body, whereby the camera (laparoscope) is positioned with the assistance of a robot that the surgical instruments guided in the operation are also in the field of view of the camera. When, however, the distance of the surgical instruments from the introduced camera is also to be regulated by the robot, then the use of a stereo camera or of a stereo laparoscope is necessary, i.e. of a camera having two optical devices.

This method, however, has the disadvantage that the instruments must always be in the field of view of the camera for the follow-up of the camera since, otherwise, the camera loses the position of the instruments. Moreover, the follow-up of the camera can be deteriorated due to contamination of the color markings (for example, with blood).

PCT Application 97/29709, "Medical Procedures and Apparatus Using Intrabody Probes", discloses a method and an apparatus wherein an instrument probe is guided through the body of a patient. The position of this instrument probe relative to another probe situated in the body of the patient is thereby determined, and the instrument probe is guided through the body based on the identified position relative to one another.

Cinquin, P. et al., "Computer Assisted Medical Interventions", IEEE Engineering in Medicine and Biology, May/June 1995, pages 254 through 263, describes computer-assisted operative interventions making use of position and shape sensors.

SUMMARY OF THE INVENTION

An object of the present invention is to provide an operation system for the implementation of surgical interventions and a method for operating such a system for the implementation of operative interventions wherein an exact, automatic positioning of the laparoscope with a robot is enabled.

This object is achieved in accordance with the invention in a method and apparatus for implementing a surgical intervention wherein a laparoscope, for visualizing the intervention, is attached to a robot arm and a position sensor is attached at the laparoscope and another position sensor is attached at a surgical instrument used in the intervention, and wherein a navigation system determines the positions of the laparoscope and the instrument on the basis of orientation information generated from the position sensors, and wherein the navigation system generates signals for automatically re-adjusting the robot arm, dependent on the identified positions, so that the surgical instrument is always located in the field of view of the laparoscope.

According to the present invention, the laparoscope introduced into the body is fully automatically controlled or re-adjusted by a robot that receives its commands from a control computer. The follow-up of the laparoscope ensues on the basis of the identified positions of the surgical instrument, so that the surgical instrument is always located in the field of view of the laparoscope.

First, the inventive, automatic camera guidance eliminates the manual camera guidance by an assistant that is subject to the described disadvantages. Second, the surgeon can concentrate fully on his/her actual task, i.e. the guidance of the surgical instruments.

The employed navigation system having sensors attached to the laparoscope and to the surgical instrument can be a matter of commercially available optical systems (for example, Polaris system of the Northern Digital company), electromagnetic systems (for example, electromagnetic Bird system of the Ascension company) or of systems based on acoustic waves.

Given employment of optical systems, care must be exercised to insure that the position sensors are extra-corporeally attached, i.e. the position sensors must be situated outside the body during the operative intervention, in order to enable a optical connection to a transmitter or, respectively, to one another.

Given electromagnetic and sound-based systems, the position sensors can be attached either extra-corporeally as well as to the tip or in the proximity of the tip of the laparoscope or of the surgical instrument.

Given extracorporeal fastening, only rigid instruments can be employed wherein the received coordinates of the extra-corporeally attached sensors are converted onto the instrument tip by means of a calibration.

Given fastening of the position sensors to the tip or in the proximity of the tip of the laparoscope or surgical instrument, the position sensors are co-introduced into the body in the intervention. This has the advantage that flexible instruments can be utilized. However, these instruments with position sensors also occupy more space in the body.

The present invention is preferably employed in minimally invasive, laparoscopic interventions.

For example, a robot of Computer-Motion, Goleta, Calif., USA, can be utilized for the robot that guides the camera.

DESCRIPTION OF THE DRAWINGS

The single FIGURE is a schematic illustration of an apparatus constructed and operating in accordance with the invention.

DESCRIPTION OF THE PREFERRED EMBODIMENTS

As shown in the FIGURE, the camera or the laparoscope 5 is introduced into the body of the patient, for example in the region of the epigastrium in FIG. 1, and is moved with a robot arm 10 with the assistance of the robot 4—the laparoscope 5 is thereby fixed to the robot arm 10 via an instrument mount 8.

The laparoscope 5 as well as one or more surgical instruments 6 are provided with position sensors 7 that generate orientation information with whose assistance the positions of the laparoscope 5 and of the surgical instrument 6 can be calculated in the navigation system 3 and forwarded to a control computer 1. The position acquisition and calculation can ensues continuously or at intervals.

The example shown in the FIGURE proceeds on the basis of an electromagnetic navigation system wherein an electromagnetic field 9 is emitted by an emitter 2 that is connected via an interface 12 to the navigation system 3 or, respectively, a central unit of the navigation system. This electromagnetic field is detected by the position sensors 7, which generate the orientation information on the basis of the electromagnetic field 9. The spatial positions and dihedral angles of the laparoscope and of the surgical instrument or instruments 6, or their spatial positions relative to one another can be very precisely detected with the assistance of the position sensors 7. These spatial positions and angle information are acquired by the control computer 1, which subsequently drives the robot 4 and thus aligns the laparoscope 5 such that all surgical instruments 6 to be monitored are in the field of view of the camera, whose images are output on a picture screen, and are thus in the field of view of the surgeon.

The present invention is suitable for employment with a mono-laparoscope (having one optics) as well as with a stereo-laparoscope (having two optics).

The control computer 1 sends the commands for the follow-up of the laparoscope 5 to the robot 4 via an interface 13. On the basis of the commands received from the control computer 1, the robot 4 re-adjusts the laparoscope 5 secured to the robot arm 10 in conformity with the movements of the surgical instrument 6 guided by the surgeon.

With the assistance of the articulated arm 10, the movement of the laparoscope 5 can ensue in six degrees of freedom: right-left, up-down, near-far, incline, tilt, turn. It is thereby possible to exclude a specific plurality of degrees of freedom. This is especially important when a movement of the laparoscope 5 in specific directions or by specific dihedral angles would jeopardize the operation safety or when the surgical instrument 6 is only guided in a specific region of the operating field.

The control computer 5 acquires the spatial positions and dihedral angles of the laparoscope 5 (camera) and of the surgical instruments 6 either continuously or at intervals on the basis of the position sensors 7 attached thereat. When the control computer 1 recognizes that laparoscope 5 and surgical instrument 6 are in positions wherein the surgical instrument 6 cannot be acquired by the camera, the control computer 1 gives the command to the robot 4 via an interface 13 (for example, serial or parallel) to move such that the surgical instrument 6 is located in the middle or in a defined region of the camera's field of view. The distance between the laparoscope 5 and the surgical instrument 6 can likewise be regulated in this way such that the distance does not downwardly or upwardly transgress a prescribable tolerance interval. The acquisition of the spatial coordinates of the laparoscope 5 and of the surgical instrument 6 and the corresponding drive of the robot arm 10 is thus executed in a servoloop.

Although modifications and changes may be suggested by those skilled in the art, it is the invention of the inventors to embody within the patent warranted heron all changes and modifications as reasonably and properly come within the scope of their contribution to the art.

What is claimed is:

1. A system for implementing a surgical intervention, comprising:
   a laparoscope for visualizing a surgical intervention, said laparoscope having a field of view;
   a robot arm to which said laparoscope is attached;
   a surgical instrument for implementing said surgical intervention;
   first and second position sensors respectively mounted at said laparoscope and at said surgical instrument for generating non-optical orientation information carried by waves selected from the group consisting of acoustic waves and non-optical electromagnetic waves; and a navigation system supplied with said orientation information from said first and second sensors for determining respective positions of said laparoscope and said surgical instrument from said non-optical orientation information, and for generating a control signal to said robot arm for automatically operating said robot arm to adjust the position of said laparoscope to constantly maintain said surgical instrument in said field of view of said laparoscope.

2. A system as claimed in claim 1 wherein said first position sensor is attached at a tip of said laparoscope and wherein said second position sensor is attached at a tip of said surgical instrument.

3. A system as claimed in claim 1 wherein said first and second position sensors are extracorporeally applied to said laparoscope and to said surgical instrument.

4. A method for adjusting a position of a laparoscope, having a field of view, attached to and movable by a robot arm for visualizing a surgical intervention conducted using a surgical instrument, comprising the steps of:

generating non-optical orientation information, originating from said laparoscope and said surgical instrument, identifying a position of said laparoscope and a position of said surgical instrument;

transmitting said non-optical orientation information from said laparoscope and said surgical instrument to a navigation system via carrier waves selected from the group consisting of acoustic waves and non-optical electromagnetic waves;

from said orientation information, determining in said navigation system the position of said laparoscope and said surgical instrument relative to each other; and dependent on said identification of said relative position, automatically electronically controlling said robot arm to re-adjust the position of said laparoscope as needed to always maintain said surgical instrument in the field of view of said laparoscope.

5. A method as claimed in claim 4 comprising employing said laparoscope and said surgical instrument in a minimally invasive surgical procedure as said surgical intervention.

* * * * *